United States Patent [19]

Kahn et al.

[11] Patent Number: 4,608,255

[45] Date of Patent: Aug. 26, 1986

[54] BIOCOMPATIBLE METHOD FOR IN SITU PRODUCTION OF FUNCTIONAL PLATELETS AND PRODUCT PRODUCED THEREBY LACKING IMMUNOGENICITY

[75] Inventors: Richard A. Kahn, St. Louis; Glenn E. Rodey, Chesterfield, both of Mo.

[73] Assignee: American National Red Cross, Washington, D.C.

[21] Appl. No.: 696,657

[22] Filed: Jan. 31, 1985

[51] Int. Cl.$^4$ .............................................. A61K 35/14
[52] U.S. Cl. ...................................... 424/101; 422/24; 435/2
[58] Field of Search .............. 424/101; 435/2; 422/24; 426/248

[56] References Cited

U.S. PATENT DOCUMENTS 2,401,131  5/1946  Bensel .................................. 422/24

OTHER PUBLICATIONS

Lawler et al.-Thrombosis Research, vol. 14(23) (1979), pp. 489–494.
Lawler-Dissert Abst. Int. B-vol. 36, No. 11 (1976), p. 5410-B.
Roshchupkin et al.-Chem. Abst., vol. 99 (1983), p. 49648a.
Slitcher et al., Jol. of American Soc. of Hematology, 1984, Abstract entitled "Blood", vol. 64, No. 5, p. 231(a).
Biffa et al., British Jol. of Dermatology, 1979, Abstract entitled "Inhibition of Human Blood Platelet Aggression . . . ", pp. 679–683.
Lau et al., Science, vol. 221, 1983, Abstract entitled "Panecreatic Islet Allograft Prolongation by Donor-Specific . . . ", pp. 754–755.
Kripke, Immunological Reviews, 1984, No. 80, Abstract entitled "Immunological Unresponsiveness Induced by UV Radiation", pp. 87–102.
Lau et al., Science, vol. 223, 1984, Abstract entitled "Prolongation of Rat Islet Allograft Survival by . . . ", pp. 607–609.
Doery et al., Blood, vol. 42, 1973, Abstract entitled "Induction of Aggregation of Human Blood Platelets . . . ", pp. 551–555.

*Primary Examiner*—Sam Rosen
*Attorney, Agent, or Firm*—Holman & Stern

[57] ABSTRACT

The present invention discloses the effect of ultraviolet (UV) radiation on platelet concentrates collected in a plastics container, particularly in a polypropylene bag. Samples irradiated at 310 nm for 30 minutes at a dose of 774 J/M$^2$ show no loss of platelet function as determined by ADP, collagen, or ristocetin-induced aggregation. Lymphocytes isolated from irradiated units are unable to act as responders or stimulators in a mixed lymphocyte reaction. The invention provides a method of UV irradiation of platelet concentrates resulting in transfusible cell suspension unable to evoke immunological response while retaining normal platelet function.

7 Claims, 2 Drawing Figures

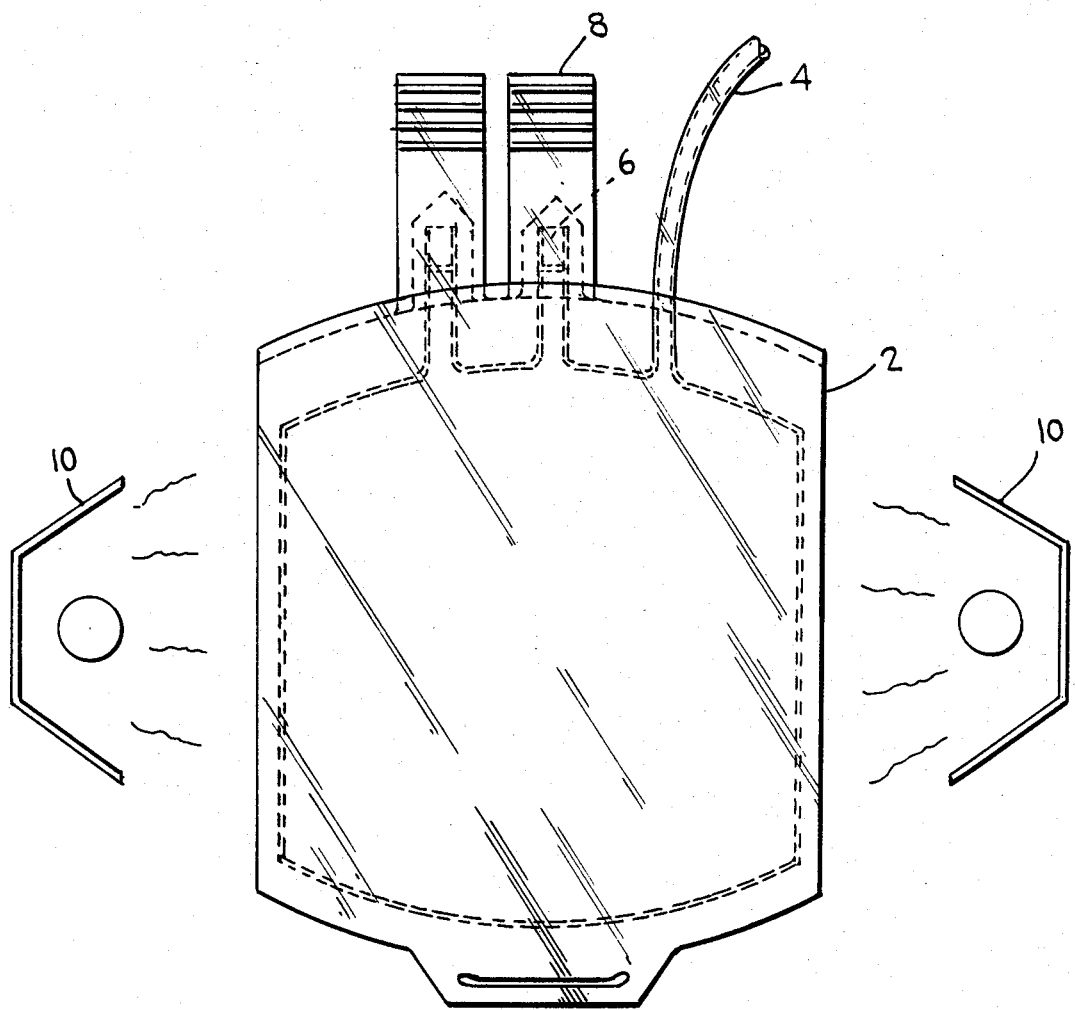

BIOCOMPATIBLE METHOD FOR IN SITU PRODUCTION OF FUNCTIONAL PLATELETS AND PRODUCT PRODUCED THEREBY LACKING IMMUNOGENICITY

BACKGROUND OF THE INVENTION

1. Technical Field

The present invention relates to transfusible, platelet preparation retaining normal, inherent platelet functions without immunogenicity. More particularly, the present invention relates to isolated, non-immunogenic, functional platelets and a container and method for preparing the same in situ.

2. Prior Art

One of the problems encountered particularly with repeated transfusions of platelet preparations is the induction of antibodies against platelets in the host or recipient. This condition is known as alloimmunization. It is generally believed that this alloimmunization is caused by the passenger lymphocytes present in the platelet concentrates prepared by the standard procedure.

Inability of UV-irradiated lymphocytes to stimulate allogenic cells in mixed lymphocyte culture has been reported by Lindahl-Kiessling et al. (Int. Arch. Allergy, 41:670-678, 1971). In addition, recent reports have shown that it is possible to induce specific immunological unresponsiveness in either an allograft (as described in Lau, et al, Science, 2211:754-756, 1983 and 223:607-609, 1984) or in animals as described by Kripke (Immunol. Rev., 80:87-102, 1984) by treatment of the transplanted tissue or recipient with UV radiation. UV radiation of an allograft may thus prevent rejection through mechanisms that retain allograft function but minimize foreignness.

As noted above, repeated platelet transfusions often result in alloimmunization (Aster et al, Transfusion, 4:428-440, 1964 and van Leeuwen, et al, Transplant. Proc., 5:1539-1542, 1973). Since platelets do not contain class II major histocompatibility antigens (Dausset, et al Transplantation, 4:182-193, 1966), which are believed to initiate the recognitive phase of the immunologic response, it is likely that the contaminating lymphocytes in platelet preparations produce the sensitization reaction (Welsh, et al, in Eur. J. Immunol., 7:267-272, 1977; Class, et al, Exp. Hematol., 9:84-89, 1981 and; Hartzmann, et al, Transplantation, 11:268-273, 1971). Prevention of platelet alloimmunization by cyclosporin treatment or by direct UV-irradiation of platelets has been recently reported by Slitcher et al, (Blood, Vol 64, No. 5, Suppl 1, 231a, 1984). However, there is no disclosure whatsoever as to the functional integrity of such UV-treated platelets as described by Slitcher et al. Furthermore, such direct exposure of platelets to UV irradiation in open containers is undesirable both because of loss of sterile conditions resulting therefrom and because of additional step of manipulation of these platelets prior to being in a condition suitable and ready for transfusion. In contrast, the process of the present invention makes it possible for the first time to obtain non-immunogenic, functional platelet concentrate ready for transfusion while kept stored in a suitable container, preferably a plastic bag, without further manipulation.

SUMMARY OF THE INVENTION

It is, therefore, an object of the present invention to provide an isolated, immunosupressed, transfusible platelet suspension in an enclosed inert, biocompatible container permeable to ultraviolet radiation, said suspension rendered immuno-deficient in situ by treatment with a source of ultraviolet radiation external and permeable to said container.

It is another object of the present invention to provide a device for in situ inactivation of immunogenic factor present in a platelet suspension enclosably held in a container comprising a container of an inert, biocompatible material suitable for passage of ultraviolet radiation therethrough from an external source thereof without affecting normal platelet function of the suspension.

It is a further object of the present invention to provide a method for obtaining transfusible platelets lacking immunogenicity.

Other objects and advantages will become evident as the detailed description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 is a schematic representation of a container in accordance with the present invention.

DETAILED DESCRIPTION OF THE INVENTION

Figure 1:
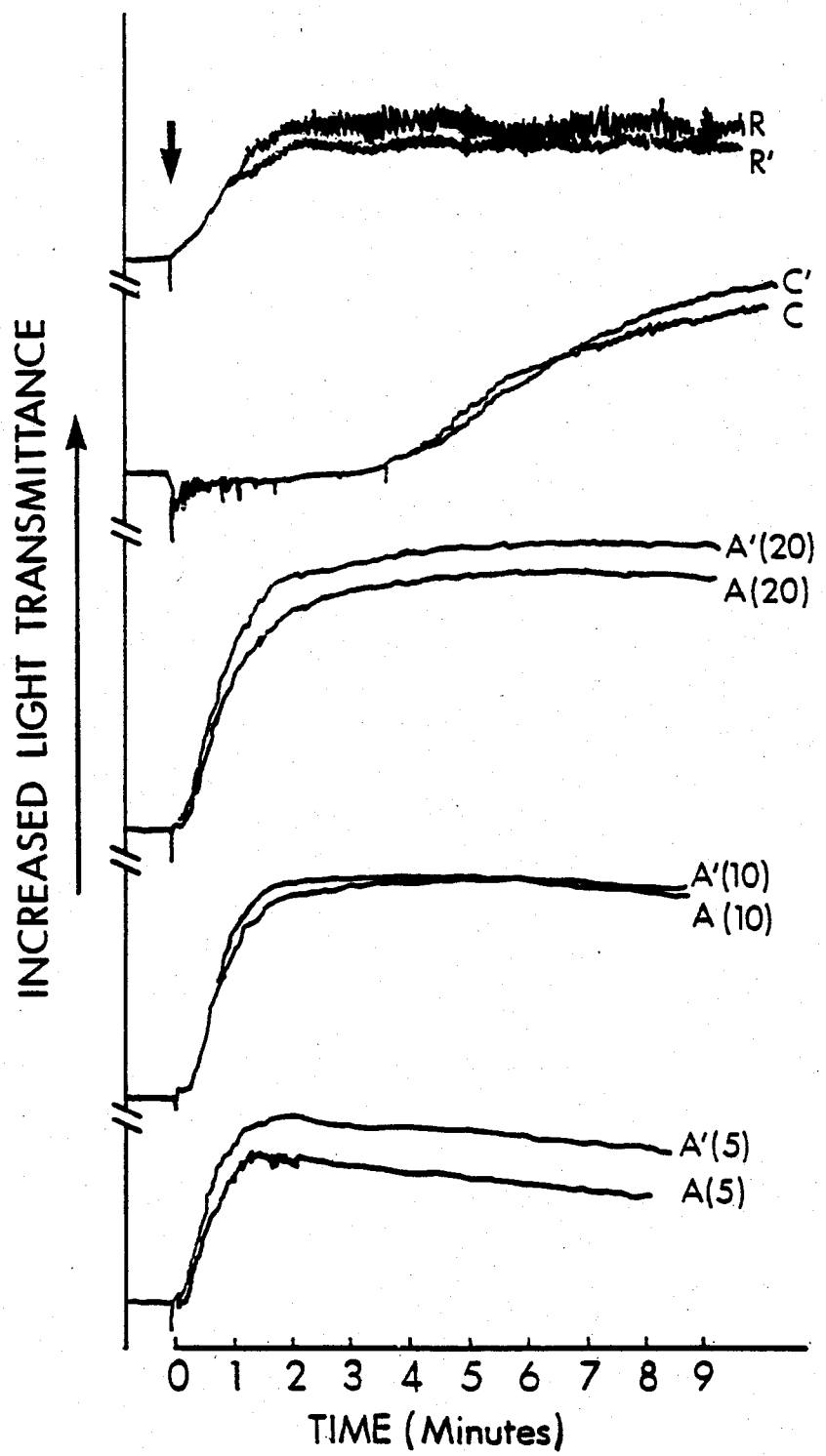
FIG. 1 shows aggregation patterns in response to agonists at final concentrations indicated. ADP at 5 $\mu$m (A5), 10 $\mu$m (A10) or 20 $\mu$m (A20). Collagen at 0.2 mg/ml (c) and ristocetin at 1.2 mg/ml (R). Both UV irradiation (1) and untreated platelets were tested at a final concentration of 250,000 $\mu$l.

These and other objects of the present invention are achieved by a device for sterile storage of platelet suspension for transfusion directly therefrom comprising a container of a biocompatible material suitable for passage of ultraviolet radiation through said material from a source external to said container whereby immunogenic factor present in said suspension is inactivated without deleterious effect on normal platelet function.

The term "functional platelet" as used herein is defined as the retention of all functions by the platelets which they normally and inherently possess. It may be emphasized here for clarity that alloimmunization induced by platelet transfusion is not believed to be due to platelets per se but due to the contaminating lymphocytes present in the routine platelet preparation. It may be further noted that the term "non-immunogenic" "immunosupressed", "immunedeficient" "immunogen-free" and the like as used herein refers to the absence or lack of sensitization reaction inducible by accessory, contaminating or antigenic factors, e.g. lymphocytes, present in the routine preparation of platelet concentrate and not due to the platelets per se.

In the practice of the present invention, any inert, biocompatible container-material suitable for collecting or storing platelets without reacting with platelets or producing deleterious or toxic effect on the function thereof and which is permeable to ultraviolet light can be used. Exemplary of the materials from which such container may be made are plastics sheets, films, bags, and the like. Preferable among the plastics material are polypropylene, polyethylene, polyvinyl chloride, cellulose acetate and polyester which have a permeability of about 86%, 80%, 63%, 71% and 26%, respectively to UV radiation. It is evident, therefore, that the dosage and length of UV exposure will have to be adjusted in accordance with the permeability. The greater the permeability, the lesser the exposure required and vice versa.

Any other type of material can also be used so long as the criteria of allowing ultraviolet light to pass through the container material and of suitability of the material for storing platelets therein without deleterious effect on the normal function thereof are satisfied. Any size, shape or thickness of the container material can be employed as long as it meets the criteria noted herein supra.

Preferred as a container (see FIG. 2) is an enclosable plastic bag (2) with inlet means (6) with a sealable or enclosing means (8) and an outlet means (4) to allow platelet suspension to pass through, e.g. for transfusion. The outlet means (4) could be disposed either at the top of the container as shown in FIG. 2 or it could be dispersed at the bottom or at any other suitable side of the container. Source of the ultraviolet radiation (10) could be disposed either on one side or on both sides of a flat type plastic bag. A source of ultraviolet radiation surrounding the plastic bag may also, of course, be employed. A means to control flow rate of the suspension through the outlet may also be provided in conjuction with the outlet means (4).

Any suitable source of ultraviolet irradiation can be employed for the practice of the present invention. Preferable is a source which emits a peak wavelength of about 310 nanometers. The dosage of the ultraviolet light (UV) and the length of exposure to UV irradiation is adjusted so that the immunogenic factor (lymphocytes) present in the platelet concentrate is abrogated while the inherent normal platelet functions are unaffected. A suitable dosage of such an UV irradiation is about 645 Joules/M$^2$ for about 10–40 minutes using polyethylene, polypropylene or polyvinyl chloride bags which are preferred.

Survival of the platelet is determined by routine survival study measured by platelets tagged with Chromium$^{51}$ or Indium$^{111}$ and determining the half-life in vivo. Satisfactory function is indicated by hemostatically effective platelets.

Other exemplary materials, methods employed for the practice of the present invention, and related tests are now described, although any equivalent or suitable substitutions thereof will, of course, be suggested to those familiar with this art. All publications mentioned hereunder are incorporated herein by reference.

MATERIALS AND METHODS

Blood cell suspensions are prepared by differential centrifugation of routine whole blood samples, e.g., donated to the American Red Cross, following standard procedure well established and known in the art. A description of such procedure can be found in 21CFR 640.20-640.27 and in Technical Manual of American Association of Blood Banks, Washington, D.C., 8th Edition 1981, pp. 47–49. The blood is collected into plastic bags containing (citrate phosphate dextrose adenine) CPDA-1 or any other suitable anticoagulant as described in 21 CFR 640.4.

Platelet concentrates (containing approximately $7 \times 10^{10}$ platelets and $1.2 \times 10^7$ lymphocytes) are prepared and are placed into a biocompatible sterile polypropylene, (EX-50, Exxon Chemical, Pottsville, Pa.) polyethylene, polyvinyl chloride or other suitable container of suitable size which easily transmits UV light. Typically, proper UV dosage is determined by using one container as the untreated control and the remaining containers or bags of concentrated platelets are irradiated while rotating on a platform rotator (American Dade, Miami, Fla.) set at 40 cycles per minute. A convenient source of irradiation is a bank of two FS-20 sun lamps (Westinghouse Electric, Pittsburgh, Pa.) which have an intensity of 425 $\mu$W/cm$^2$ measured 5 cm from the source (determined by a UVX-Radiometer, Ultra-Violet Products, San Gabriel, Calif.) at a mean wavelength of 310 nm (UV-B). Immediately following irradiation, platelet aggregation studies in vitro are performed, and lymphocyte viability is ascertained in a standard six day mixed lymphocyte reaction (MLR) to determine that proper UV dosage has been achieved as described by Hartzmann, et al, Transplantation, 11:268–273, 1971, and incorporated herein by reference.

Platelet aggregation is studied using a dual-channel Payton Aggregometer (Model 800B, Payton Asso., Scarborough, Ontario, Canada). Irradiated and control samples are diluted with untreated, autologous platelet-free plasma so that the final platelet concentration is about 250,000/$\mu$l. The suspension is then exposed to either adenosine diphosphate (ADP), collagen (both reagents were obtained from American Dade Corp., Miami, Fla.) or ristocetin (Helena Labs., Beaumont, Tex.) and the resulting aggregation recorded.

The MLR test is performed on mononuclear cells isolated from platelet suspensions. Separation is accomplished by decantation of the contents of the bag into sterile plastic tubes, dilution of the suspension with 35 ml of phosphate buffered saline (PBS), followed by centrifugation to obtain a cell pellet. The pellet is then resuspended in PBS layered over 10 ml of 30% isotonic Percoll (Pharamacia Fine Chemicals, Piscataway, N.J.) and centrifuged at 200$\times$g for 20 minutes to remove platelets. After a second resuspension in 20 ml PBS, the remaining cells are laid over 10 ml of ficoll hypaque and centrifuged at 400$\times$g for 30 minutes to pellet contaminating RBC's. Mononuclear cells (80% lymphocytes) are then harvested from the interface, washed 3 times in PBS, and resuspended in RPMI 1640 medium (Rosewell Park Memorial Institute, Buffalo, N.Y.) containing 25 mM HEPES (N-2-hydroxyethylpiperazine-N-2-ethanesulfonic acid) buffer, 100 mM L-glutamine, 0.05 mg/ml gentamycin sulphate and 10% heat inactivated human serum. The final cultures contain about 50,000 responder cells and about 50,000 gamma irradiated stimulator cells (irradiated with 3000 rads) in a total volume of 200 $\mu$l well.

Lymphocytes are tested in parallel MLR's both as responders and stimulators with two normal allogenic lymphocyte suspensions and as responder cells to a 1/100 dilution of pokeweed mitogen (Gibco, Grand Island, N.Y.). Triplicate cultures are established in 96-well round bottom microtiter trays (Flow Labs., McClean, Va). After 132 hours of culture at 37° C. in a 5% CO$_2$ humidified atmosphere, all wells are pulsed with 1.0 uCi $^3$H-thymidine, incubated for an additional 18 hours, and the lymphoproliferation of each well counted for radioactivity. Results are expressed as the stimulation index (SI), which is the mean experimental counts per minute (CPM) of triplicate determinations divided by the mean control counts, and as the actual CPM of thymidine uptake.

Experiments can also be performed on pure lymphocyte suspensions to determine the dose range of UV irradiation which would abrogate the MLR. After determing suitable UV dosage, platelet concentrates are then irradiated at the same dose range to determine the effect of UV iradiation on platelet function. Table I shows the results of such a test. It should be noted that after 10 minute irradiation of a platelet concentrate, resulting in a UV dose of 258 $J/M^2$, the capacity of passenger lymphocytes to act as either stimulators or responders in the MLR is greatly reduced. After 25 minutes of UV irradiation, lymphocyte activity is completely abrogated (i.e. S.I. < 1.0). In only one of six tests did lymphocytes irradiated for 25–30 minutes respond to pokeweed mitogen with an S.I greater than the autologous control.

FIG. 1 shows that UV irradiation for 30 minutes has no discernible effect on platelet number or function. Exposure of irradiated concentrates to 5, 10, or 20 $\mu$m ADP, 0.2 mg/ml collagen, or 1.2 mg/ml ristocetin results in aggregation patterns virtually identical in response time, slope, and maximal aggregation achieved compared to the untreated platelets.

The present invention for the first time provides a system whereby platelet concentrate can be collected and held in storage and rendered immuno-incompetent in situ while retaining essential platelet function by simple treatment with an external source of UV without additional manipulation of the collected platelet concentrate. It is quite evident that the system and method of the present invention opens a new vista in transfusion technology and clinical practice utilizing irradiated platelet concentrates or products as taught by the present disclosure.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated, immunogen-free, transfusible platelet suspension in an enclosed, inert, biocompatible container permeable to ultraviolet radiation, said platelet suspension being biologically functional and having been rendered free of immunogenicity in situ by treatment with an effective amount of ultraviolet radiation external to and permeable through said container.

2. A container enclosably containing an in situ ul-

TABLE I

MLR OF LYMPHOCYTES DERIVED FROM UV IRRADIATED[1] PLATELET CONCENTRATES

A. Ability to Stimulate in the MLR

| Number of Experiments | Time (minutes) | Dose ($J/m^2$) | Allo-geneic[2] | Auto-logous[2] | Mean S.I.[3] ± 1 S.D. | S.I. Range |
|---|---|---|---|---|---|---|
| 8 | 0 | | 28,750 | 2100 | 23.8 ± 23.6 | 6.0–84.6 |
| 3 | 10 | 258 | 8,164 | 1832 | 4.3 ± 3.3 | 0.9–9.3 |
| 3 | 15 | 387 | 4,549 | 1832 | 2.5 ± 2.0 | 1.0–6.4 |
| 7 | 20 | 216 | 5,257 | 2118 | 3.6 ± 3.8 | 0.3–11.7 |
| 5 | 25 | 645 | 2,634 | 2261 | 2.1 ± 1.7 | 0.3–4.8 |
| 5 | 30 | 774 | 1,331 | 2261 | 0.8 ± 0.6 | 0.3–1.9 |

B. Ability to Respond in the MLR

| Number of Experiments | Time (minutes) | Dose ($J/m^2$) | Allogeneic Response | | | | Pokeweed Mitogen Response | | | |
|---|---|---|---|---|---|---|---|---|---|---|
| | | | Allo-geneic[2] | Auto-logous[2] | Mean S.I.[3] ± 1 S.D. | S.I. Range | Mitogen[2] | Autologous[2] | Mean S.I. ± S.D. | S.I. Range |
| 7 | 0 | — | 28,236 | 1856 | 19.0 ± 13.2 | 5.7–48.5 | 24,983 | 1856 | 21.7 ± 14.8 | 3.9–47.1 |
| 2 | 10 | 258 | 1,552 | 833 | 1.8 ± 1.1 | 1.0–3.3 | 2,911 | 833 | 3.2 ± 0.9 | 2.5–3.8 |
| 2 | 15 | 387 | 394 | 833 | 0.5 ± 0.3 | 0.1–0.7 | 925 | 833 | 1.0 ± 0.3 | 0.8–1.2 |
| 7 | 20 | 516 | 1,270 | 1856 | 0.7 ± 1.0 | 0.0–3.9 | 6,485 | 1856 | 3.5 ± 4.8 | 0.1–13.5 |
| 5 | 25 | 645 | 509 | 2265 | 0.3 ± 0.2 | 0.0–0.8 | 3,501 | 2265 | 2.6 ± 3.1 | 0.0–6.0 |
| 5 | 30 | 774 | 187 | 2265 | 0.1 ± 0.1 | 0.0–0.2 | 807 | 2265 | 0.7 ± 1.3 | 0.0–3.0 |

[1]Exposure to UV-B (290–320 nm) radiation 5 cm from the source for times indicated.
[2]Mean CPM
[3]Stimulation index = CPM of stimulated culture/CPM of autologous culture These results clearly demonstrate that it is possible to treat platelet concentrates held in an enclosed container with external source of UV light and completely abolish the ability of the passenger lymphocytes to act as responders or stimulators in an MLR while retaining normal platelet function. The mechanism by which UV radiation exerts its effect on lymphocytes is unclear.

There are only a few published reports on the effect of UV irradiation on platelets. Doery et al (Blood, 42:551–555, 1973) showed that UV irradiation at wavelengths less than 302 nm induced aggregation of washed platelets in the presence of added fibrinogen. Maximal aggregation was seen at 248 nm; however, UV irradiation at 313 nm had no effect. Other investigators, e.g., Briffa, et al (Brit. J. Dermat. 101:679–683, 1979) have shown that collagen induced aggregation was inhibited only after 120 minute UV exposure to irradiation (wavelength of 320–400 nm).

traviolet-irradiated, transfusible, functional platelet suspension lacking immunogenicity, said container being made of an inert, biocompatible material suitable for passage of ultraviolet radiation therethrough from a source external to said container.

3. The container of claim 2 wherein said container is formed of a material selected from the group consisting of polypropylene, polyethylene and polyvinyl chloride.

4. A method of in situ producing functional platelets lacking immunogenicity in a container containing platelets comprising collecting a platelet suspension in an inert, biocompatible, sterile, closed container made of a material suitable for passage of ultraviolet radiation therethrough and then irradiating said platelet suspension with an external source of ultraviolet radiation capable of penetrating through said container for a time and at a dosage level sufficient to inactivate immunogenic factors present in said suspension without affecting platelet function.

5. The method of claim 4 wherein said container is formed of plastics material selected from the group consisting of polypropylene, polyethylene and polyvinyl chloride.

6. The method of claim 5 wherein the dosage of said radiation is about 645 Joules/$M^2$ for about 10–40 minutes.

7. A transfusible platelet suspension lacking immunogenicity produced by the method of claim 6.

* * * * *